United States Patent [19]

Hidaka et al.

[11] Patent Number: 4,987,148

[45] Date of Patent: Jan. 22, 1991

[54] BIOCIDAL 4,5-DICHLORO-1,2-DITHIOL-3-ONE COMPOSITION

[75] Inventors: Yasuhiro Hidaka, Osaka; Masato Magami; Takeshi Inoue, both of Oita; Sumio Nakane, Kyoto, all of Japan

[73] Assignee: Yoshitomi Pharmaceutical Industries, Ltd., Osaka, Japan

[21] Appl. No.: 424,029

[22] Filed: Oct. 19, 1989

Related U.S. Application Data

[63] Continuation-in-part of Ser. No. 298,433, Jan. 18, 1989, abandoned.

[30] Foreign Application Priority Data

Jan. 19, 1989 [JP] Japan .................................. 63-9401

[51] Int. Cl.$^5$ ...................... A01N 43/26; A01N 43/36
[52] U.S. Cl. ...................... 514/441; 514/424
[58] Field of Search ............................... 514/424, 441

[56] References Cited

U.S. PATENT DOCUMENTS

| | | |
|---|---|---|
| 3,894,149 | 7/1975 | Mast ...................... 514/86 |
| 3,903,273 | 9/1975 | Mast ...................... 514/132 |
| 4,289,581 | 9/1981 | Katayama et al. ................... 162/161 |
| 4,334,957 | 6/1982 | Katayama et al. ................... 162/161 |
| 4,595,679 | 6/1986 | Broadbent ...................... 514/67 |
| 4,647,577 | 3/1987 | Umekawa et al. ................... 514/441 |

OTHER PUBLICATIONS

Mitsubishi Chemical Industries, Ltd., Catalogue.
Hawley, The Condensed Chemical Dictionary 9th Ed., pp. 306, 307 & 577.
World Patent Index (Derwent), No. 77-33799 Y/19 (Japanese Patent Examined Publication (Kokoku), No. 14294/1977.
World Patent Index (derwent), No. 80-35216C/20 (Japanese Patent Examined Publication (Kokoku), No. 23721/1987.

*Primary Examiner*—Allen J. Robinson
*Attorney, Agent, or Firm*—Sughrue, Mion, Zinn, Macpeak & Seas

[57] ABSTRACT

A biocidal composition which comprises 4,5-dichloro-1,2-dithiol-3-one and N-methyl-2-pyrrolidone in a proportion by weight of 70:30 to 10:90 is described.

2 Claims, No Drawings

BIOCIDAL 4,5-DICHLORO-1,2-DITHIOL-3-ONE COMPOSITION

This is a continuation in-part of U.S. patent application Ser. No. 07/298,433 filed on Jan. 18, 1989, now abandoned.

BACKGROUND OF THE INVENTION

This invention relates to biocidal 4,5-dichloro-1,2-dithiol-3-one compositions which are excellent in solubility and stability in storage and easy to handle.

4,5-Dichloro-1,2-dithiol-3-one (hereinafter referred to as dithiol compound) is the compound of the formula (I):

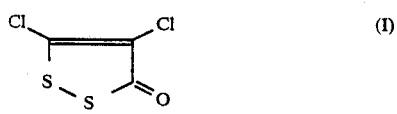

in yellow crystalline powders, m.p. 61° C. which has been used as an excellent slime control agent for industrial cooling water, washing water, raw water and power water (Japanese Patent Examined Publication (Kokoku) No. 14294/1977). The dithiol compound, produced in powdery form, is extremely difficult to handle during the production work since it is highly skin-irritant. Besides, such powdery form is very inconvenient in handling the product thereof.

Therefore, it is considered to be advantageous and convenient in workability, safety, storability, transportability and dispersibility in use to make the powders into liquid preparations.

Particularly, it is economic to permit the liquid preparations of these industrial microbicidal compounds to contain the effective ingredient at as high concentration as possible for transportation and storage thereof. Moreover, these liquid preparations are required to have high stability during transportation and storage.

However, the dithiol compound itself is a sparingly water-soluble substance having a solubility in water of below 1%, and thus it cannot be made an aqueous solution of high concentration. Furthermore, the dithiol compound is very unstable in the obtained aqueous solution and susceptible to hydrolysis in a short period of time. Thus, such an aqueous solution cannot be put into practical use.

In the specification of U.S. Pat. No. 4647577, as the research for making a liquid preparation of the dithiol compound, there are disclosed liquid preparations which are obtained by dissolving the dithiol compound in a haloacetic acid ester as the solvent, which is hydrophobic (lipophilic) solvent. However, when 1,2-bis(bromoacetoxy)ethane among the haloacetic acid esters, is used as a solvent, the solubility of the dithiol compound is about 22%. The liquid preparations having such an extent of solubility cannot be regarded as ones of sufficiently high concentration in terms of transportation economy.

In Japanese Patent Examined Publication (Kokoku) No. 23721/1987, there are disclosed liquid preparations which are obtained by dissolving the dithiol compound in a mixed solvent of diethylene glycol monomethyl ether and dimethylformamide. The solubility of the dithiol compound in this solvent is about 67 weight % at 25° C., which is very high and the obtained liquid preparations are pretty sufficient in respect of the solubility of the dithiol compound. However, dimethylformamide is inherently so strong in toxicity that it is problematic to use it in a large amount as a solvent. Also, these liquid preparations are insufficient to storage and stability of the dithiol compound over a long period. Besides, liquid preparations containing the dithiol compound at a high concentration have defects that, when they are exposed to a low temperature in transportation or storage, crystallization occurs followed by the solidification of the whole liquid preparations. These solidified products are so hard that it is difficult to even take them out of the vessel thereof and it is necessary to redissolve them by heating for utilizing. This is highly disadvantageous in work and thermal economy.

On the other hand, U.S. Pat. No. 4,595,679 discloses the use of pyrrolidone compounds such as N-vinyl-2-pyrrolidone, N-methyl-2-pyrrolidone and 2-pyrrolidone, as an emulsifying agent or a solvent for an insecticidal composition, and that the use of pyrrolidone compound increases the penetration of the insecticide into the body of the insect to provide enhanced insect knockdown.

SUMMARY OF THE INVENTION

Thus, the present inventors conducted intensive study for the purpose of solving the above-mentioned subjects. As a result, they have found that it was possible to obtain the compositions which are excellent in solubility, as well as storage and stability of the dithiol compound and easy to handle by using N-methyl-2pyrrolidone as the solvent, which has led to the completion of the present invention.

That is, the present invention relates to a biocidal composition characterized by containing 4,5-dichloro-1,2-dithiol-3-one and N-methyl-2-pyrrolidone, which are excellent in solubility as well as storage and stability, and easy to handle.

DETAILED DESCRIPTION OF THE INVENTION

In accordance with the compositions of the present invention, a high concentration-dithiol compound solution can be obtained, and also, solidification seldom occurs when they are exposed to a low temperature during transportation and storage, and should they be solidified, they become at worst solidified materials in sherbet form which is soft enough to be taken out easily by scooping. The solidified materials in sherbet form are mixtures of N-methyl-2-pyrrolidone and the dithiol compound which are partially frozen, and can be easily separated from the vessel and subdivided. Such a property of the product being easily taken out of the vessel is particularly referred to as scoopability. The compositions of the present invention may possibly be solidified at a low temperature, but even in that case, they, unlike the solidified products obtained so far, become solidified materials in sherbet form which are good in scoopability and are comparatively easy to redissolve. Therefore, the compositions of the present invention can be fully used even as the solidified products.

For the compositions of this invention, the dithiol compound and N-methyl-2-pyrrolidone can be mixed in a suitable proportion, preferably in a weight proportion ranging from 70:30 to 10:90, more preferably in a weight proportion ranging from 70:30 to 15:85 of the dithiol compound relative to N-methyl-2-pyrrolidone.

In producing the compositions of this invention, the usual dissolving and mixing methods are applicable. For example, the dithiol compound in powdery form is dissolved in N-methyl-2-pyrrolidone under stirring to afford a liquid composition. From operational viewpoint, the dissolution is preferably conducted in a closed system.

For the purpose of obtaining the high concentration-dithiol compositions, the dissolution is preferably conducted under heating. Both ingredients in liquid form can be mixed after heating to a temperature higher than the melting point of the dithiol compound.

The compositions obtained in accordance with the present invention can be used as the industrial microbicidal/microbistatic compositions as they are or by mixing and/or diluting with solvents or surfactants usually used in this field.

As the solvents, there can be mentioned amides such as dimethylformamide and diethylformamide; ethers such as ethylene glycol monomethyl ether, ethylene glycol monoethyl ether, ethylene glycol monophenyl ether and diethylene glycol monomethyl ether; alcohols or glycols such as isopropyl alcohol, diethylene glycol, dipropylene glycol or polypropylene glycol and ketones such as acetone or methyl isobutyl ketone. Two or more species of these solvents can be used in combination. Examples of the surfactants are nonionic ones such as alkylolamides and polyoxyethylene polyoxypropylene alkyl ethers or cationic surfactants such as trimethylacetyl ammonium chloride. Particularly the alkylolamides surfactants to be used in this invention include fatty acid alkylolamides synthesized from a fatty acid and an alkylolamine (see "Synthesis of Surfactants and Application of group" pp. 150-151, Oda and Teramura, Maki Shoten, published on June 30, 1975), preferably, those obtained by reaction of the fatty acids which are higher fatty acids having 8 to 18 carbon atoms with ethanolamines or diethanol amines.

The thus-obtained industrial microbicidal/microbistatic compositions can be used for microbicidal/microbistatic purposes, for various systems such as process water in papermaking process, industrial cooling water, washing water, heavy oil sludges, cutting oils, lignin-containing waste liquors, water paints, antifouling paints, latexes, textile oils and other liquid targets. For example, when they are used in papermaking process water, though the amount of the compositions of this invention to be used varies depending upon the state of adhesion of slime, the kind of slime-forming bacteria and so forth, the compositions are usually used at a concentration in the range from 1 to 100 ppm, preferably within the range from 5 to 50 ppm to attain microbicidal/microbistatic effects.

The compositions obtainable in accordance with this invention have the following characteristic merits.

(1) They have the solubility of about 70 weight % at room temperature (25° C.), (2) The stability of the dithiol compound as the effective ingredient in the composition is extremely high in the storage and stability tests (at 60° C., for 30 days), (3) They are seldom solidified at a low temperature, and even when solidified, they become solidified preparations in sherbet form with excellent scoopability which enables easy separation and subdivision thereof, (4) These solidified preparations in sherbet form are comparatively easy to redissolve, (5) N-Methyl-2-pyrrolidone causes few problems in terms of odor, inflammability, toxicity and so forth, and permits preparation of compositions having high operability and safety.

Thus, the compositions of this invention have characteristics which have not been found in any of the previous compositions, and they are excellent in solubility as well as storage and stability and easy to handle.

Specifically, the preferable compositions of the present invention which are easy to handle in production, transportation and storage thereof and excellent in stability can be obtained by mixing dithiol compound with N-methyl-2-pyrrolidone in a weight proportion ranging from 70:30 to 10:90, more preferably in a weight proportion ranging from 70:30 to 15:85.

The present invention is explained below by illustrating experimental examples and working examples, which are not to be construed as limitative, needless to say.

EXPERIMENTAL EXAMPLE 1

Solubility test

The solubilities (weight %) of the dithiol compound in 100 g of the respective solvents shown in Table 1 at 25° C. ar indicated in Table 1.

TABLE 1

| Solvent | Amount by weight of dissolved dithiol compound (g) | Solubility (weight %) |
| --- | --- | --- |
| N-Methyl-2-pyrrolidone | 222 | 68.9 |
| 1,2-Bis(bromoacetoxy)ethane | 28 | 21.9 |
| Dimethylformamide containing 5 weight % diethylene glycol monomethyl ether | 206 | 67.3 |
| N-Vinyl-2-pyrrolidone | 117 | 53.9 |
| 2-Pyrrolidone | 104 | 51.0 |

EXPERIMENTAL EXAMPLE 2

Storage and stability tests

In transparent 50 ml-glass vessels, a 50% N-methyl-2-pyrrolidone composition of the dithiol compound (the composition of the present invention), a 50% dimethylformamide composition containing 5 weight % diethylene glycol monomethyl ether, a 50% N-vinyl-2-pyrrolidone composition and a 50% 2-pyrrolidone composition of the dithiol compound (compositions for comparison) were prepared, and the storage and stability tests were conducted.

The tests were conducted by leaving the compositions standing at 60° C. for 15 days and 30 days and examining the remaining rate of the dithiol compound based upon the measurement of area ratio at 317 nm by means of high performance liquid chromatography (HPLC). The results are shown in Table 2.

TABLE 2

| Solvent | Remaining percentage of dithiol compound | |
| --- | --- | --- |
| | 15 days (%) | 30 days (%) |
| N-Methyl-2-pyrrolidone | 97.3 | 93.3 |
| Dimethylformamide containing 5 weight % diethylene glycol monomethyl ether | 94.2 | 84.7 |
| N-Vinyl-2-pyrrolidone | — | — |

TABLE 2-continued

| Solvent | Remaining percentage of dithiol compound | |
|---|---|---|
| | 15 days (%) | 30 days (%) |
| 2-pyrrolidone | 38.9 | 18.0 |

Note: N-Vinyl-2-pyrrolidone composition of the dithiol compound could not be obtained since exothermic polymerization reaction occurred intensively in a few minutes after the mixing the dithiol compound with N-vinyl-2-pyrrolidone.

As apparent from the Table 2, the dithiol compound as the effective ingredient in the composition of the present invention was scarcely decomposed even after the composition was left standing for 15 days and 30 days, and is excellent in storage and stability as compared with compositions for comparison.

EXPERIMENTAL EXAMPLE 3

Crystallization and redissolution test

In transparent 50 ml-glass vessels, the dithiol compound and N-methyl-2-pyrrolidone were mixed at the prescribed concentrations, and dissolved, if necessary, under heating. The crystals were yielded by cooling these solutions suitably, under the observation of the state. The crystallizing temperature was measured. The crystallized solutions were heated, and the temperature at which the crystals began to dissolve was measured. The results are shown in Table 3.

TABLE 3

| Concentration of dithiol compound in N-methyl-2-pyrrolidone (weight %) | Crystallizing temperature (°C.) | Crystals-dissolving temperature (°C.) |
|---|---|---|
| 10 | −29.3 | −23.7 |
| 20 | −27.8 | −22.7 |
| 30 | −22.0 | −16.2 |
| 40 | −18.8 | −9.2 |
| 50 | −18.3 | 4.7 |
| 60 | −13.3 | 12.0 |
| 70 | 6.0 | 26.5 |
| 80 | 26.8 | 36.2 |

As evident from the Table 3, the compositions of the present invention, though they are compositions of an extremely high concentration of about 70 weight %, exist in liquid form at room temperature. Furthermore, even in case they are solidified, they exist as solidified preparations in sherbet form which are excellent in scoopability, without the hard solidification of the whole liquid preparation. Besides, these solidified materials can be redissolved at a comparatively low temperature.

EXPERIMENTAL EXAMPLE 4

Storage and stability tests

The dithiol compound and N-methyl-2-pyrrolidone were mixed at the concentrations as shown in Table 4 to prepare compositions. Each 50 ml of the compositions was served in a polyethylene bottle, and the bottle was further served tightly in a can with a lid.

The storage and stability tests were conducted by leaving the compositions standing at 60° C. for 11 days (or 15 days) and 30 days in the above state and examining the remaining rate of the dithiol compound based upon the measurement of area ratio at 317 nm by means of high performance liquid chromatography (HPLC). The results are shown in Table 4.

TABLE 4

| Concentration of dithiol compound in N-methyl-2-pyrrolidone (%) | Remaining percentage of dithiol compound | |
|---|---|---|
| | 11 days (%) | 30 days (%) |
| 5 | 70.8 (15 days) | 58.3 |
| 10 | 90.5 | 83.2 |
| 15 | 93.7 | 87.4 |
| 20 | 93.8 | 88.2 |
| 25 | 94.3 | 89.0 |
| 30 | 95.6 | 88.8 |
| 35 | 95.7 | 89.3 |
| 40 | 96.6 | 90.4 |
| 50 | 97.3 (15 days) | 93.3 |

Since the decomposition rate of the dithiol compound fit to the first order reaction, a half life of the dithiol compound ($t_{\frac{1}{2}}$), in the each compositions at 60° C., was calculated with the following equation:

$$-\ln\alpha = kt$$

wherein $\alpha$ represents a remaining percentage of the dithiol compound, k represents a decomposition rate constant of the dithiol compound and t represents a number of days. The results are shown in Table 5.

TABLE 5

| Concentration of dithiol compound in N-methyl-2-pyrrolidone (%) | Half life of dithiol compound (day) |
|---|---|
| 5 | 39 |
| 10 | 103 |
| 15 | 145 |
| 20 | 153 |
| 25 | 165 |
| 30 | 174 |
| 35 | 181 |
| 40 | 209 |
| 50 | 300 |

As apparent from the above Tables 4 and 5, the half life of the diothol compound exceeds 100 days in the case of the composition having a concentration of 10% or more, thus, such compositions are sufficiently stable in viewpoint of a transportation economy.

Accordingly, the present invention provides the compositions which are excellent in solubility and stability during storage and transportation of the dithiol compound, and easy to handle, by employing the ratio of dithiol compound and N-methyl-2-pyrrolidone of ranging from 70:30 to 10:90, more preferably from 70:30 to 15:85.

In the compositions of the below-mentioned examples 1 to 6, neither crystallization nor solidification was found even after a long period of storage, and they could be handled in liquid state stably.

When the compositions of Examples 7 to 11 were used as slime control agents, they exhibited excellent microbicidal effects, inhibiting increase in number of viable microbes in industrial cooling water, washing water, raw water, power water and so forth.

The formulation examples of the composition of the present invention will be shown hereunder as Examples.

| Example 1 | |
|---|---|
| 4,5-Dichloro-1,2-dithiol-3-one | 70% |
| N-Methyl-2-pyrrolidone | 30% |

| -continued | |
|---|---|
| Example 2 | |
| 4,5-Dichloro-1,2-dithiol 3-one | 50% |
| N-Methyl-2-pyrrolidone | 50% |
| Example 3 | |
| 4,5-Dichloro-1,2-dithiol-3-one | 40% |
| N-Methyl-2-pyrrolidone | 60% |
| Example 4 | |
| 4,5-Dichloro-1,2-dithiol-3-one | 20% |
| N-Methyl-2-pyrrolidone | 80% |
| Example 5 | |
| 4,5-Dichloro-1,2-dithiol-3-one | 15% |
| N-Methyl-2-pyrrolidone | 85% |
| Example 6 | |
| 4,5-Dichloro-1,2-dithiol 3-one | 10% |
| N-Methyl-2-pyrrolidone | 90% |
| Example 7 | |
| 4,5-Dichloro-1,2-dithiol-3-one | 7% |
| N-Methyl-2-pyrrolidone | 3% |
| Diethylene glycol monomethyl ether | 89% |
| Trimethylcetylammonium chloride | 1% |
| Example 8 | |
| 4,5-Dichloro-1,2-dithiol-3-one | 5% |
| N-Methyl-2-pyrrolidone | 5% |
| Diethylene glycol monomethyl ether | 89% |
| Trimethylcetylammonium chloride | 1% |
| Example 9 | |
| 4,5-Dichloro-1,2-dithiol-3 one | 5% |
| N-Methyl-2-pyrrolidone | 5% |
| Diethylene glycol monomethyl ether | 88% |
| Polyoxyethylene polyoxypropylene alkyl ether | 2% |
| Example 10 | |
| 4,5-Dichloro-1,2-dithiol-3-one | 2% |
| N-Methyl 2-pyrrolidone | 8% |
| Diethylene glycol monomethyl ether | 88% |
| Polyoxyethylene polyoxypropylene alkyl ether | 2% |
| Example 11 | |
| 4,5-Dichloro-1,2-dithiol-3-one | 1% |
| N-Methyl-2-pyrrolidone | 9% |
| Diethylene glycol monomethyl ether | 89% |
| Trimethylcetylammonium chloride | 1% |

As is apparent from the above-described experimental examples and examples, higher concentration-4,5-dichloro-1,2-dithiol-3-one compositions than those with conventional solvents can be obtained by using N-methyl-2-pyrrolidone as the solvent. Further, the storage and stability of 4,5-dichloro-1,2-dithiol-3-one as the effective ingredient of the compositions of the present invention is extremely high and even when the compositions are solidified, they come to be in sherbet form and can be used as they are or through redissolution easily. Moreover, they cause few problems in terms of toxicity, odor and inflammability, and are very useful as a microbicidal composition.

The present invention has been described in detail in the foregoing specification including Examples, which can be modified and varied to such an extent as not to conflict with the concept and the scope of the present invention.

What is claimed is:

1. A biocidal composition with high storability and stability, which comprises 4,5-dichloro-1,2-dithiol-3-one and N-methyl-2-pyrrolidone in a proportion by weight of 70:30 to 10:90.

2. A biocidal composition with high storability and stability, which comprises 4,5-dichloro-1,2-dithiol-3-one and N-methyl-2-pyrrolidone in a proportion by weight of 70:30 to 15:85.

* * * * *